United States Patent [19]

Roberts et al.

[11] Patent Number: 5,238,819
[45] Date of Patent: Aug. 24, 1993

[54] DIAGNOSTIC ASSAY FOR THE DETECTION OF PREECLAMPSIA

[75] Inventors: James M. Roberts, Mill Valley; Robert N. Taylor, San Francisco, both of Calif.

[73] Assignee: The Regents of the University of California, Oakland, Calif.

[21] Appl. No.: 689,066

[22] PCT Filed: Dec. 13, 1989

[86] PCT No.: PCT/US89/55600

§ 371 Date: Jun. 10, 1991

§ 102(e) Date: Jun. 10, 1991

Related U.S. Application Data

[63] Continuation-in-part of Ser. No. 284,212, Dec. 14, 1988, abandoned.

[51] Int. Cl.$^5$ .............................. C12Q 1/02
[52] U.S. Cl. ..................... 435/29; 436/63; 436/86; 436/65
[58] Field of Search ............ 435/29; 436/63, 65, 436/510; 530/350

[56] References Cited

FOREIGN PATENT DOCUMENTS

89/05560 5/1990 PCT Int'l Appl. .

OTHER PUBLICATIONS

Spargo, et al., "Glomelular capillary endotheliosis in toxemia of pregnancy," *AMA Arch. Pathol.* 68:593–597 (1959).
Redman, et al., "Factor VIII consumption in preeclamsia," *Lancet* 2:1249–1252 (1977).
Dadak, et al., "Morphological changes in the umbilical arteries of babies born to preeclamptic mothers: an ultrastructural study," *Placenta* 5:419–426 (1984).
Roberts, J. M., "Pregnancy-related hypertension," in *Maternal-Fetal Medicine-Principles and Practice*, Creasy, R. K. and Resnick, R., eds., W. B. Saunders, Philadelphia, (1984) pp. 703–752.
Stubbs, et al., "Plasma fibronectin levels in preeclampsia: a possible biochemical marker for vascular endothelial damage," *Am. J. Obstet. Gynecol.* 150:885–887 (1984).
Rodgers, et al., "Preeclampsia is associated with a serum factor cytotoxic to human endothelial cells," *Am. J. Obstet. Gynecol.* 159:908–914 (1988).
Musci, T. J., et al., "Mitogenic activity is increased in the sera of preeclamptic women before delivery," *Am. J. Obstet. Gynecol.* 159(6):1446–1451 (1988).
Keski–Oja, J., et al., "Transforming Growth Factors and Control of Neoplastic Cell Growth," *J. Cell. Biochem.* 33:95–107 (1987).
Cagnoli, L., et al., "Lymphocyte Hyporesponsiveness During Edema, Proteinuria and Hypertension (EPH) Gestosis," *La Ricerca Clin. Lab.* 11:229–238 (1981).
Gaugas, J. M., et al., "Complement Fixing Antibody Against Solubilized Placental Microsomal Fraction in Pre-Eclampsia Sera," *Br. J. exp. Path.* 55:570–574 (1974).
Redman, C. W. G., et al., "Plasma Urat and Serum Deoxycytidylate Deaminase Measurements for the Early Diagnosis of Pre-Eclampsia," *Br. J. Obstet. Gynecol.* 84:904–908 (Dec. 1977).
Chemical Abstracts General Subject Index—11th Collective (1982–1986) p. 25973GS.
Musci et al., —*Am. J. Obstet. & Gynecology* vol. 159 (Dec. 1988) pp. 1446–1451.
Westley et al.,—*J. Biological Chemistry* vol. 259(16) Aug. 1984 pp. 10030–10035.

*Primary Examiner*—Sam Rosen
*Attorney, Agent, or Firm*—Townsend and Townsend Khourie and Crew

[57] ABSTRACT

This invention relates to the diagnosis of preeclampsia using an assay to measure a mitogenic factor in blood. Preeclampsia is a serious problem in pregnant women. It is an idiopathic life threatening hypertensive condition. The condition of preeclamptic women can often deteriorate to a point where serious injury will occur to either the mother, child or both. Preeclampsia is a leading cause of death both maternal and infant.

9 Claims, 2 Drawing Sheets

DIAGNOSTIC ASSAY FOR THE DETECTION OF PREECLAMPSIA

The government has rights in this invention pursuant to NIH Contract No. HD24180 awarded by the National Institute of Health.

This application derives from PCT application U.S. Ser. No. 89/05560 filed on Dec. 13, 1989 and is a continuation-in-part of U.S. Ser. No. 07/284,212 filed Dec. 14, 1988, now abandoned.

BACKGROUND OF THE INVENTION

Field of the Invention

This invention relates to the diagnosis of preeclampsia using an assay to measure a mitogenic factor in blood. Preeclampsia is a serious problem in pregnant women. It is an idiopathic life threatening hypertensive condition. The condition of preeclamptic women can often deteriorate to a point where serious injury will occur to either the mother, child or both. Preeclampsia is a leading cause of death both maternal and infant.

Information Disclosure

Preeclampsia occurs in 7-10% of pregnancies and is responsible for significant maternal and fetal morbidity (Roberts, J. M., Pregnancy-related hypertension. In: Creasy, R. K.; Resnick R., eds., Maternal-Fetal Medicine-Principles and Practice, Philadelphia: W. B. Saunders, 1984, 703-752). Despite decades of interest and research, the pathogenesis of this disease is still poorly understood. Recent evidence, however, suggests that endothelial cell injury may play an important role in the preeclamptic syndrome. The histopathological findings of endothelial lesions in renal and umbilical vessels obtained from preeclamptic patients have been recognized (Spargo, B. H.; McCartney, C. P.; Winemiller, R., Glomerular capillary endotheliosis in toxemia of pregnancy. AMA Arch. Pathol., 1959, 68:593-497; Dadak C., Ulrich W., Sinzinger H. Morphological changes in the umbilical arteries of babies born to preeclamptic mothers: an ultrastructural study. Placenta 1984, 5:419-426). Lately, several reports have documented biochemical abnormalities in serum from preeclamptic patients which support the concept that endothelial cell perturbation and sublethal injury of these cells may contribute to the pathogenesis of preeclampsia. Most of these studies have been indirect, showing elevated levels of endothelial cell products in serum (e.g., fibronectin (Stubbs, T. M.; Lazarchick, J.; Horger, E. O., III, Plasma fibronectin levels in preeclampsia: a possible biochemical marker for vascular endothelial damage. Am. J. Obstet. Gynecol, 1984, 150:885-887), factor VIII antigen (Redman, C. W. G.; Beilin, L. J.; Stirrat, G. M., et al., Factor VIII consumption in preeclampisa. Lancet 1977, II:1249-1252), or platelet and coagulation abnormalities (Roberts, J.M., Pregnancy-related hypertension, In: Creasy, R. K.; Resnick, R., eds., Maternal-Fetal Medicine-Principles and Practice. Philadelphia: W. B. Saunders, 1984, 703-752). We have recently demonstrated directly that serum from preeclamptic women injures endothelial cells in vitro (Rodgers, G. M.; Taylor, R. N.; Roberts, J. M., Preeclampsia is associated with a serum factor cytotoxic to human endothelial cells, Am. J. Obstet. Gynecol, 159:908-914, 1988).

Figure 1A:
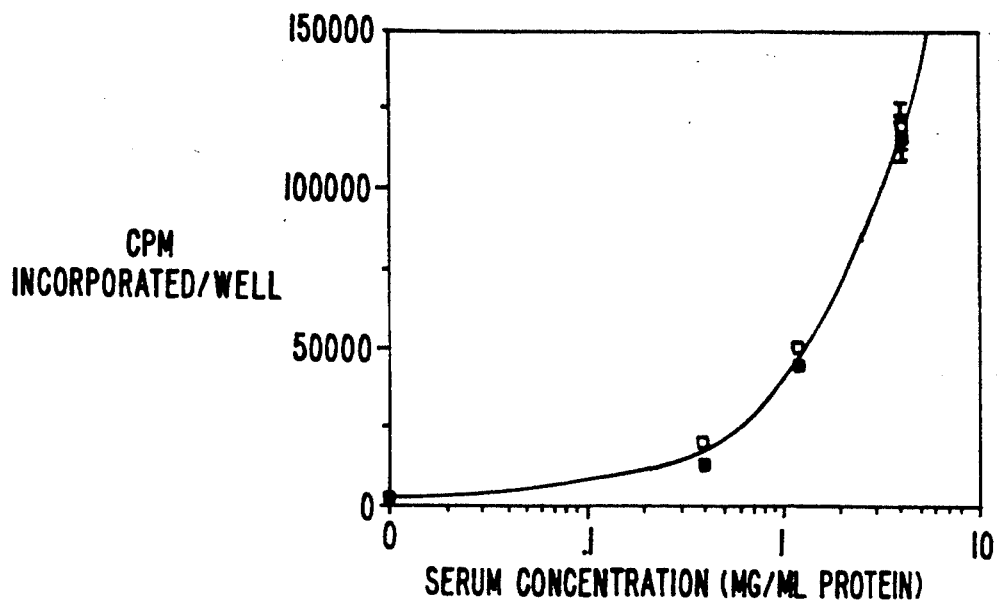
FIG. 1

Mitogenic dose-response of cultured fibroblasts exposed to serum from normal and preeclamptic patients. Quiescent fibroblasts were incubated with paired pre- and postpartum sera from normal and preeclamptic patients as described in Materials and Methods. Incorporation of $^3$H-thymidine into fibroblast DNA increased in a dose-dependent, logarithmic fashion. Shown are mitogenic activities of prepartum (open box) and postpartum (closed box) sera from normal (A) and preeclamptic (B) patients. There was a significant left-shift of the curve for prepartum as compared to postpartum preeclamptic serum but not in paired sera from normal pregnancy ($P<0.01$).

FIG. 2

Mitogenic activity of sera from normal and preeclamptic patients. (A) Direct comparison of prepartum sera from preeclamptic and normal patients diluted to a final concentration of 2% demonstrated a 46% increase in mitogenic activity in preeclamptic sera as compared to normal ($P<0.01$). (B) Serum collected at 24-48 hours postpartum revealed no difference between the two groups ($P>0.6$).

FIG. 3

No indirect effect of magnesium sulfate ($MgSO_4$) treatment on the mitogenic activity of sera from preeclamptic patients. Two groups of preeclamptic patients were compared. One group (n=4) had received intravenous $MgSO_4$ prior to the prepartum blood sample collection. In the other group (n=4), blood specimens were collected before treatment with $MgSO_4$. The percent mitogenic stimulation (pre-/post- $\times 100$) values were not different ($P>0.6$).

SUMMARY OF THE INVENTION

This invention relates to the discovery of a mitogenic factor present in the blood of preeclamptic women. This factor is a proteineous compound of about 160 kDa. This factor permits the prediction, detection and diagnosis of preeclampsia. It is capable of stimulating fibroblast mitosis. However, this factor is heat and acid labile in sera when the sera is measured for mitogenic activity after acidification or heating.

Also described herein is a diagnostic assay for the prediction and detection of preeclampsia comprising the in vivo detection of mitogenic activity in blood from pregnant women. The assay can be direct or indirect. This assay is particularly disclosed wherein the mitogenic activity is detected using either fibroblast or smooth muscle cells. More particularly, the assay can comprise the detection of mitogenic activity by monitoring the uptake of radiolabelled thymidine by cells directly stimulated to begin mitosis.

It is preferred that the blood being assayed be fractionated into serum or plasma samples.

There is also disclosed herein an in vitro method for detecting preeclampsia comprising measuring mitogenic activity of blood from women with preeclampsia. More specifically this method can involve the direct assay of mitogenic activity of fibroblast or smooth muscle cells. The method preferably uses human cells. Most specifically disclosed is a method for detecting radiolabelled thymidine uptake by cells activated by the sera or plasma of preeclamptic women.

A kit for assaying for mitogenic activity in blood from preeclamptic women is also described herein. The kit will comprise instructions, negative and positive controls, means for direct or indirect measurement of mitogenic activity such as cell culturing means and means for quantifying or measuring the mitogenic activity of the blood.

DETAILED DESCRIPTION OF THE PREFERRED EMBODIMENTS

This invention involves the discovery that mitotic stimulating compounds are present in preeclamptic women. The sera of these women differ significantly in mitogenic activity in standard assays for the detection of mitosis. The presence of such activity forms the basis of the diagnostic assays disclosed herein.

Characteristics of the Mitogenic Factor

The mitogenic factor is a proteinaceous compound of approximately 160 kDa. This factor has a demonstrated sensitivity to protease. In addition, sera containing this factor loses its mitogenic activity below a pH of 3.0 (as tested after reneutralization of the sera). The factor has a negative charge at neutral pH. The component is also heat sensitive. When sera is heated, the factor is mitogenically inactivated after 1 hr. at 60° C. Purification of this factor can be achieved using standard protein purification techniques which include sizing gels, selective precipitation by salt, ion exchange columns and the like.

Sample Collection

The described assays preferably use a serum or plasma sample. Arterial or venous blood can be used. It is preferred that the samples be taken from a vein. The blood should be centrifuged within 10 hrs and the plasma or serum fraction collected. The assays can be performed on fresh or frozen samples. The mitogenic activity is stable at $-70°$ degrees C. for up to 4 months.

Samples may be taken between 3 months and before termination of the pregnancy. It is an advantage of this invention that mitotic activity precedes the hypertensive condition.

In Vitro Assays for Mitogenic Activity

A number of different assays have been described for measuring mitogenic activity. A review of these assays can be found in Keski-Oja, J., et al., Transforming Growth Factors and Control of Neoplastic Cell Growth, J. Cell. Bioch., 33:95-107, 1987. Typically these assays measure some function accompanying the transition of cells from the resting state into the replication state. Such functions include:

1. The incorporation of tritiated thymidine into cellular DNA.
2. The stimulation of DNA synthesis, measured by total DNA concentrations using the chromogenic dye diphenylamine.
3. Cellular proliferation measured by increases in cell number as measured using a hemocytometer or coulter cell counter.
4. Stimulation of anchorage-independent growth, as measured by cell colony formation in soft agar.

It is particularly convenient to measure thymidine uptake which directly reflects DNA synthesis.

Mammalian cells for which cell culturing parameters have been described are of primary use herein. Typically these cells are susceptible to mitogenic stimulation and include murine and human cells. It is preferred that the cells used in the described assays be derived from human tissues. Most preferably fibroblast or smooth muscle cells, in our tests human endothelial cells were not sensitive to the mitogenic compound described herein.

A kit for the direct measuring of mitogenic activity would include instructions, negative controls from normal blood, positive controls derived from patients with preeclampsia and cells sensitive to mitogenic stimulation. Culturing means for growth of cells would include, media and sterile culture flasks. A labeled nutrient or other means for measuring mitosis may also be included.

Indirect Measurement

In addition to the direct measurement of mitogenic activity, it is possible to assay for the mitogenic activity indirectly. Indirect mitogenic activity involves the measuring of the specific blood factor associated or responsible for activating mitogenesis in the in vitro assays. Methods for identifying and quantifying the mitogenic factor include HPLC, electrophoretic separations and immunoassays. Immunoassays are preferred and a multitude of standard immunoassays are available for indirect measurement. These include competitive immunoassays such as ELISA, IRMA (immunoradiometric assay) and RIA. The indirect method of detection has the advantage of being quicker, less expensive and readily incorporated into routine diagnostic use.

Any of the above assays can be designed to function as an assay in the disclosed invention.

Prediction of Preeclampsia

The preeclamptic condition is predicted by a statistically significant elevation in the levels of mitogenic factor as early as the second trimester of pregnancy. This elevation can be detected months before the onset of the clinical manifestations of preeclampsia.

A prospectively collected group of women were followed during their pregnancy. Serial plasma samples were collected, diluted to 2%, and analyzed for mitogenic activity using the human foreskin fibroblast cell assay described below. Comparisons of thymidine uptake by the cells were made for four preeclamptic and six normal control primigravidae. Comparisons were made using the Mann-Whitney test with the results of each patient's plasma mitogenic activity normalized to her immediate postpartum sample. For analysis, the normalized predelivery values for each patient were reduced to averages, overall and separately for each trimester. The overall averaged data indicated that women predestined to meet strict American College of Obstetrics and Gynocology (ACOG) criteria for the diagnosis of preeclampsia had significantly elevated pre- to post-delivery ratios of plasma mitogenic (growth) factor activity throughout pregnancy, as compared to prospectively sampled normal primigravidae ($1.7 \pm 0.2$ vs. $0.8 \pm 0.1$, mean $\pm$SEM, $P<0.005$). Similar statistical analyses of averaged mitogenic activity for each trimester appeared to distinguish women destined to develop preeclampsia from their normal peers as early as the second trimester ($2.0 \pm 0.4$ vs. $0.8 \pm 0.1$, $P<0.005$).

The following examples illustrate the functionality of the invention described herein. The examples are not to be construed as a limitation on the claims. It being further understood that non-critical variations in procedures by those of skill are possible.

EXAMPLES

Serum Samples

Serum samples are obtained from pregnant patients with and without preeclampsia. Venous blood samples were collected in most cases.

Cell Culture

Human foreskin fibroblasts (passages 10 through 20) were obtained from the U.C.S.F. Cell Culture Facility and maintained in culture using a growth medium of Dulbecco's Modified Eagle's Medium (DMEM) with 4.5 g/liter glucose supplemented with 10% fetal calf serum, penicillin/streptomycin (100 U/ml) and fungizone (500 ng/ml), at 37° C. in a humidified atmosphere and 5% $CO_2$. Cells were plated at a density of $5 \times 10^4$ cells per well in 24-well Falcon dishes, grown to confluence and then maintained in a quiescent state with serum-free medium for 48 to 72 hours prior to exposure to patient serum. Serum-free medium was prepared using DMEM but supplemented with 20 mM HEPES, insulin (1 $\mu$g/ml), transferrin (0.5 $\mu$g/ml), and bovine serum albumin (500 $\mu$g/ml, Sigma), in place of fetal calf serum.

Thymidine Incorporation Assay

Mitogenic activity of serum was determined by measuring the incorporation of $^3$H-thymidine into nascent DNA by fibroblasts as described by DiCorleto and Bowne-Pope (DiCorleto, P. E.; Bowen-Pope, D. F., Cultured endothelial cells produce a platelet-derived growth factor-like protein, Proc. Natl. Acad. Sci. U.S.A., 83, 80:1919–1923). Briefly, aliquots of patients' sera were added to triplicate wells containing confluent quiescent fibroblast cultures to yield a final serum concentration of 2% (final protein concentration $\pm SD = 1.5 \pm 0.4$ mg/ml). After 20 hours of incubation, $^3$H-thymidine (0.5 $\mu$Ci/well, 15.7 Ci/mmol, New England Nuclear) were added to each well and labeling was carried out for 4 hours. Thymidine incorporation into 10% trichloracetic acid insoluble nucleic acid was determined by scintillation counting.

Mitogenic activity was expressed either as total cpm $^3$H-thymidine incorporated per well of confluent fibroblasts or as percent mitogenic stimulation. The latter was defined as (cpm incorporated predelivery)/(cpm incorporated postdelivery) $\times 100$. All values were expressed as the mean $\pm$ SE of triplicate assays.

Protein Determination

Protein concentrations of the serum samples were quantified by the method of Bradford (Bradford, M. M., A rapid and sensitive method for the quantitation of microgram quantities of protein utilizing the principle of protein dye binding, Anal. Biochem. 1976, 72:248–254).

Statistics

Evaluations of statistical significance were performed using analysis of variance and Students' t-test (two-tailed analysis) where appropriate. Tests with $P < 0.01$ were considered to reflect significant differences.

Patients

Consecutive patients were recruited from admissions to the Obstetrical Service of the Medical Center at the University of California, San Francisco (UCSF). All had term, singleton gestations and the diagnosis of preeclampsia was made based on the following criteria: no prior history of hypertension or renal disease; a rise in blood pressure of at least 30 mm Hg systolic or 15 mm Hg diastolic, or if these were not known a blood pressure of at least 140 mm Hg systolic or 90 mm Hg diastolic (manifested on two readings at least 6 hours apart); and proteinuria of $\geq 1 + (\sim 30$ mg/dl) urine protein on a catheterized specimen. Normal, control patients had no history of hypertension; were normotensive throughout gestation; and had no proteinuria (Table I). Edema was not used to define preeclampsia for inclusion in this study. Mean arterial pressure (MAP) was calculated from the average of blood pressure readings taken from admission to delivery (MAP = diastolic + [systolic - diastolic]/3).

Serum Samples

Venous blood samples were collected in early labor and again at 24–48 hours postpartum in accordance with a protocol approved by the UCSF Committee on Human Research. The serum fraction was separated by centrifugation and stored frozen for up to four months at $-70°$ C. prior to assay.

Results

A. Comparison of Mitogenic Activities of Pre- and Postpartum Serum

Figure 1B:
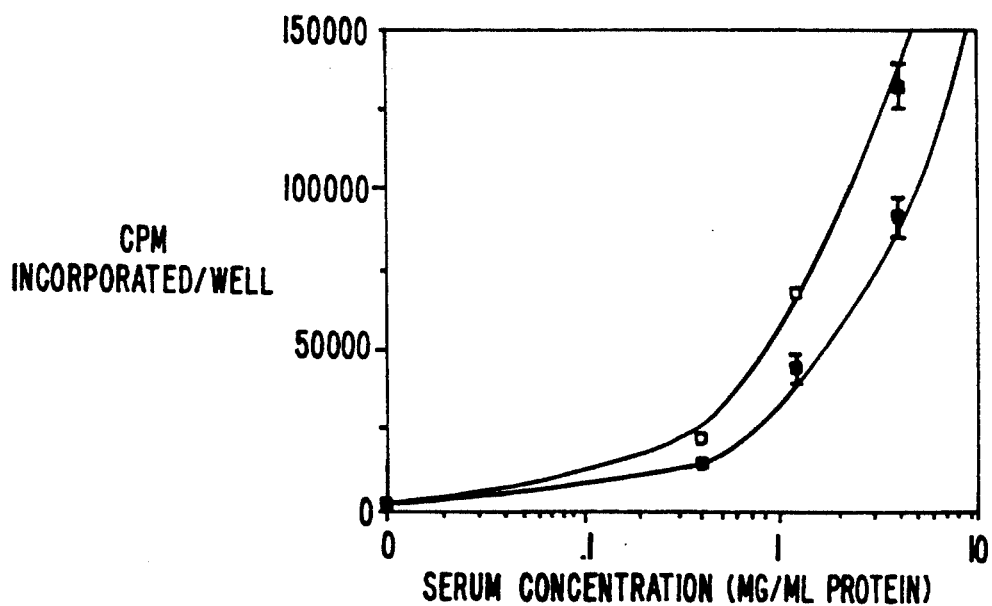

Initial studies were performed to determine the mitogenic effect of increasing concentrations of serum on human foreskin fibroblasts in culture. There was a dose dependent increase in $^3$H-thymidine incorporation from 0.04 to 4 mg/ml serum protein. No difference in mitogenic potency was seen in paired sera from normal parturients (FIG. 1A). However, matched pre- and postpartum specimens from preeclamptic patients showed a significant left-shift of the dose response curve in the prepartum specimens as compared to post-delivery samples ($P < 0.01$ for serum concentrations greater than 1 mg/ml protein, FIG. 1B). These data defined the range of serum protein concentrations that allowed differences to be detected in the subsequent cross-sectional analyses. Experiments comparing a larger number of patients were done at a fixed, final serum concentration of 2% (final serum protein concentration $\pm SD = 1.5 \pm -/0.4$ mg/ml). Paired pre- and postpartum serum samples of 13 preeclamptic and 10 control parturients were compared and normalized using the postpartum value for each patient. Percent mitogenic stimulation (pre-/post- $\times 100$) was significantly increased in paired preeclamptic sera (mean$\pm$SE = 107$\pm$6%; $P < 0.01$). The coefficient of variation of the thymidine incorporation assay was 12%. No changes in serum-induced mitogenic activity were observed even after multiple freeze-thaw cycles.

MITOGENIC ACTIVITY IN PREPARTUM SERUM

Figure 2A:
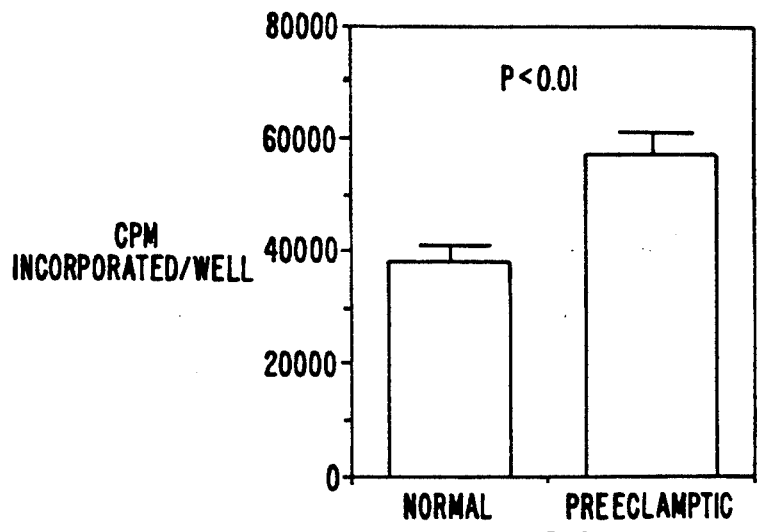
Figure 2B:
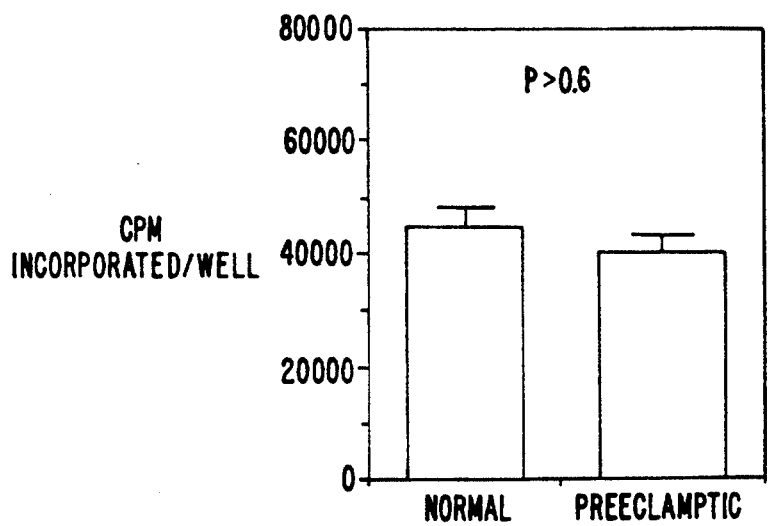

In order to determine whether the elevated mitogenic stimulation seen in paired preeclamptic sera was due to greater prepartum activity or decreased postpartum activity, or both, comparisons of antepartum and postpartum sera were performed. Direct comparison of prepartum sera from 15 preeclamptic and 14 normal patients showed a 46% increase in the mean level of thymidine incorporation of the preeclamptic specimens [over the amount in normal specimens ($P < 0.01$, FIG. 2a). However, in a separate experiment, direct comparison of postpartum sera collected 24–48 hours after delivery revealed no significant difference in mitogenic activity between normal and preeclamptic patients (n=12, FIG. 2B).

EFFECT OF MAGNESIUM SULFATE ON MITOGENIC ACTIVITY

Figure 3:
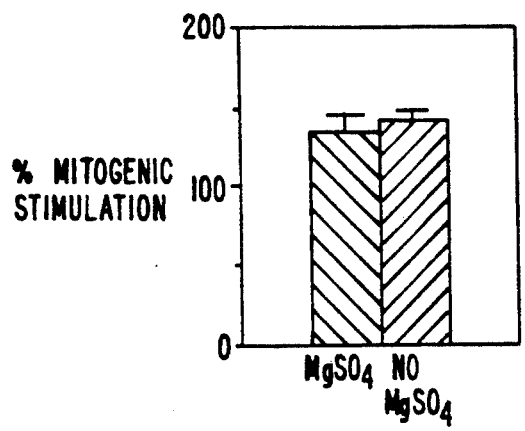

We addressed the possibility that increased mitogenic activity in preeclamptic vs. normal sera might be secondary to magnesium sulfate (MgSO4) therapy administered uniformly to preeclamptic patients at our institution. The direct addition of MgSO4 at concentrations of 2 and 6 mg/dl (levels comparable to serum levels in treated patients) to control predelivery serum, did not affect the incorporation of $^3$H-thymidine by these samples (P>0.6, Table II). To determine whether differences in mitogenic activity between patient groups could be attributed to an indirect effect of MgSO4 treatment, paired pre- and postpartum sera from two groups of preeclamptic patients were compared. One group (I, n=4) had received intravenous MgSO4 prior to the prepartum blood sample collection. In the other group (II, n=4), specimens were collected before treatment with MgSO4. The percent mitogenic stimulation values were (Group I: mean ±SE=135±9.5%; Group II: mean ±SE=141±5.9%, P>0.6; FIG. 3).

TABLE I

| PATIENT DATA | | |
|---|---|---|
| | NORMAL (n = 14) | PREECLAMPTIC (n = 15) |
| Gestational Age (weeks) | 39.5 ± 1.5 | 38.5 ± 1.9 |
| Mean Arterial Pressure (mm Hg) | 84 ± 3.1 | 107 ± 10.7* |
| Urine Protein (mg/dl) | 0–trace | 30–300 |
| Uric Acid (mg/dl) | ND} | 5.6 ± 1.8 |
| Platelets (K/ml) | ND§ | 261 ± 65 | values are expressed as mean ± SD
*P < 0.1
ND = not determined
} normal value at 27–40 weeks = 4.4 ± 0.8 mg/dl
§ normal value (non-pregnant) = 150–400 K/ml

TABLE II

| NO DIRECT EFFECT OF MgSO4 ON MITOGENIC ACTIVITY OF SERUM | | | |
|---|---|---|---|
| MgSO4 added (mg/dl) | 0 | 2 | 6 |
| $^3$H-thymidine incorporated/well (cpm ± SE) | 42,723 ± 3,046 | 42,540 ± 3,360 | 41,257 ± 2,438 |

Legend

Quiescent human fibroblasts were incubated for 24 hours in the presence of 2% serum from a normal, prepartum woman, supplemented with 0, 2, or 6 mg/dl (final concentration in the serum) magnesium sulfate (MgSO4). $^3$H-thymidine uptake was determined in triplicate as described in Materials and Methods. Analysis of variance revealed no differences between the three treatments (P>0.6).

What is claimed is:

1. A diagnostic assay for the detection and prediction of preeclampsia comprising (a) collecting blood samples from pregnant women; and (b) detecting mitogenic activity of the blood and wherein elevated levels of mitogenic activity indicate a preeclamptic condition.

2. An assay of claim 1 wherein the detecting of mitogenic activity is achieved by measuring mitosis in animal cells selected from the group consisting of fibroblast and smooth muscle cells.

3. An assay of claim 2 wherein serum or plasma samples are prepared from the blood and wherein mitogenic activity is detected by exposing the animal cells to the serum or plasma samples.

4. A diagnostic assay of claim 2 wherein the detecting step (b) comprises measuring radiolabeled thymidine uptake by the animal cells exposed to the samples.

5. A method for the diagnosis of preeclampsia comprising (a) collecting blood from a pregnant woman; and (b) detecting a mitogenic factor in the blood wherein said factor has a molecular weight of about 160 kDA, a proteinaceous component, is protease sensitive, having a negative charge at neutral pH capable of stimulating fibroblast mitosis and exhibiting, when present in sera, acid and heat lability with respect to its mitogenic activity and wherein elevated levels of mitogenic activity indicate a preeclamptic condition.

6. A method of claim 5 wherein detecting of mitogenic activity further comprises the measuring of mitogenic activity in animal cells selected from the group consisting of fibroblast and smooth muscle cells exposed to the blood.

7. A method of claim 6 wherein the mitogenic activity is measured by detecting radiolabeled thymidine uptake by cells activated by the sera.

8. A method of claim 6 wherein serum or plasma samples are prepared from the blood and wherein mitogenic activity is detected by exposing the animal cells to the serum or plasma samples.

9. A kit for the diagnosis of preeclampsia comprising: a container containing human cells, said cells responsive to mitogenic activity in blood from women with preeclampsia, a container containing radiolabeled thymidine and a container containing the mitogenic factor derived from the blood of preeclamptic women.

* * * * *